United States Patent
Bai et al.

(10) Patent No.: US 11,283,029 B2
(45) Date of Patent: Mar. 22, 2022

(54) THERMALLY ACTIVATED DELAYED FLUORESCENCE MATERIAL, ORGANIC ELECTROLUMINESCENT DEVICE, AND DISPLAY PANEL

(71) Applicant: Wuhan China Star Optoelectronics Semiconductor Display Technology Co., Ltd., Wuhan (CN)

(72) Inventors: Yamei Bai, Wuhan (CN); Xianjie Li, Wuhan (CN); Jinchang Huang, Wuhan (CN); Yu Gu, Wuhan (CN); Lin Yang, Wuhan (CN); Jiajia Luo, Wuhan (CN)

(73) Assignee: Wuhan China Star Optoelectronics Semiconductor Display Technology Co., Ltd., Wuhan (CN)

(*) Notice: Subject to any disclaimer, the term of this patent is extended or adjusted under 35 U.S.C. 154(b) by 355 days.

(21) Appl. No.: 16/488,599

(22) PCT Filed: Jun. 20, 2019

(86) PCT No.: PCT/CN2019/092074
§ 371 (c)(1),
(2) Date: Aug. 26, 2019

(87) PCT Pub. No.: WO2020/155525
PCT Pub. Date: Aug. 6, 2020

(65) Prior Publication Data
US 2020/0251662 A1 Aug. 6, 2020

(30) Foreign Application Priority Data
Jan. 31, 2019 (CN) .................. 201910098498.2

(51) Int. Cl.
H01L 51/50 (2006.01)
H01L 51/00 (2006.01)
C07D 413/10 (2006.01)
C09K 11/06 (2006.01)
H01L 51/52 (2006.01)

(52) U.S. Cl.
CPC ........ H01L 51/0072 (2013.01); C07D 413/10 (2013.01); C09K 11/06 (2013.01); H01L 51/0035 (2013.01); H01L 51/0036 (2013.01); H01L 51/0037 (2013.01); H01L 51/0067 (2013.01); H01L 51/0071 (2013.01); C09K 2211/1018 (2013.01); H01L 51/5016 (2013.01); H01L 51/5056 (2013.01); H01L 51/5072 (2013.01); H01L 51/5088 (2013.01); H01L 51/5092 (2013.01); H01L 51/5206 (2013.01); H01L 51/5221 (2013.01); H01L 2251/301 (2013.01); H01L 2251/308 (2013.01)

(58) Field of Classification Search
None
See application file for complete search history.

(56) References Cited

U.S. PATENT DOCUMENTS

2017/0256723 A1* 9/2017 Wang .................. C07D 413/10

* cited by examiner

Primary Examiner — Gregory D Clark

(57) ABSTRACT

A thermally activated delayed fluorescence (TADF) material including a compound represented by formula (I). The TADF material can be applied to an organic light-emitting layer, thereby realizing a series of high-performance TADF electronic devices.

19 Claims, 2 Drawing Sheets

THERMALLY ACTIVATED DELAYED FLUORESCENCE MATERIAL, ORGANIC ELECTROLUMINESCENT DEVICE, AND DISPLAY PANEL

RELATED APPLICATIONS

This application is a National Phase of PCT Patent Application No. PCT/CN2019/092074 having International filing date of Jun. 20, 2019, which claims the benefit of priority of Chinese Patent Application No. 201910098498.2 filed on Jan. 31, 2019. The contents of the above applications are all incorporated by reference as if fully set forth herein in their entirety.

FIELD AND BACKGROUND OF THE INVENTION

The present invention relates to a field of organic electroluminescent technology and, more particularly, to a thermally activated delayed fluorescence material, an organic electroluminescent using same, and a display panel using same.

Organic light-emitting diodes (OLEDs) are exceptional in terms of self-illumination, luminescence efficiency, viewing angles, response times, temperature adaptation ranges, manufacturing process, drive voltage, power consumption, body type, flexibility, and application prospect. Therefore, the OLEDs have been spotlighted by many researchers.

Guest luminescent materials play a vital role in OLED devices. The guest luminescent materials used in early OLED devices are fluorescence materials. The OLED devices based on the fluorescence materials can only achieve 25% internal quantum efficiency (IQE) at most because the branching ratio of singlet and triplet excitons is 1:3 in the OLED devices. As a result, applications of fluorescent electroluminescent devices are limited.

Phosphorescent materials are able to harvest both singlet and triplet excitons to achieve 100% IQE due to spin-orbit coupling of heavy metals. However, the phosphorescent materials generally contain a rare metal element such as Ir or Pt. Furthermore, the lack of green light-emitting materials is a bottleneck of the phosphorescent materials.

Thermally activated delayed fluorescence (TADF) materials can realize relatively small energy gap between the lowest singlet and triplet excited states ($\Delta E_{ST}$) by changing molecular structures of the TADF materials. A singlet excited state is generated from the triplet excited state by reverse intersystem crossing (RISC), and the singlet excited state is converted into light emission. That is, the TADF materials are able to realize 100% IQE by simultaneously using the singlet excitons and the triplet excitons.

Fast RISC and high photoluminescence quantum yield (PLQY) are required conditions of the TADF materials. Nowadays, compared to the phosphorescent materials, there is a lack of TADF materials satisfying the above required conditions. Moreover, not only the phosphorescent materials but the TADF materials are lacking in green light-emitting materials.

Consequently, there is a need to provide a new TADF material to fill a blank of the green light-emitting materials.

SUMMARY OF THE INVENTION

An object of the present invention is to provide a thermally activated delayed fluorescence (TADF) materially, in particular a green light-emitting TADF material. Specifically, in the present invention, a green light-emitting TADF material having small energy gap between the lowest singlet and triplet excited states ($\Delta E_{ST}$), high photoluminescence quantum yield (PLOY), and fast reverse intersystem crossing (RISC) is provided. Furthermore, the green light-emitting TADF material is applied to an organic light-emitting layer of an organic electroluminescent device to obtain a series of high-efficiency organic light-emitting diodes (OLEDs According to one aspect of the present invention, a TADF material is provided including a compound represented by the following structural formula (1):

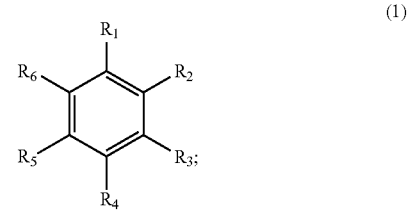

(1)

wherein $R_1$ to $R_6$ each independently represents a methyl group, an electron acceptor group represented by the following structural formula (A-i), or an electron donor group:

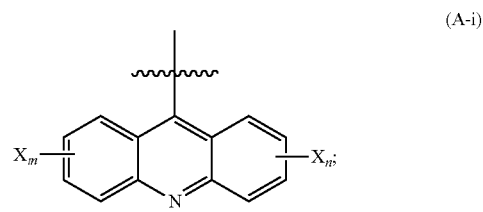

(A-i)

wherein X is a halogen atom, and m and n each independently represents an integer from 1 to 4;

wherein the electron donor group is a substituted or unsubstituted phenoxazinyl group; and wherein the compound includes at least one electron acceptor group and at least one electron donor group.

In one preferred embodiment, the TADF material comprises the compound represented by one of the following structural formulas (i-1 to i-13):

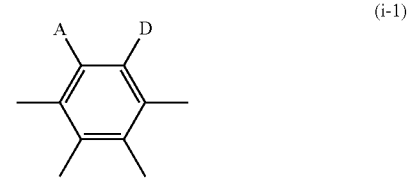

(i-1)

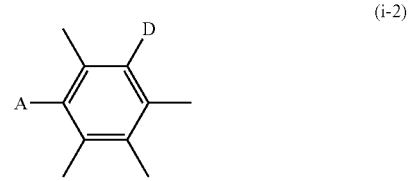

(i-2)

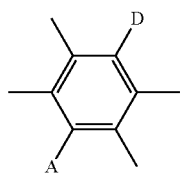
(i-3)
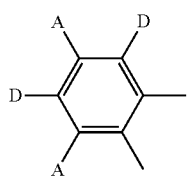
(i-4)
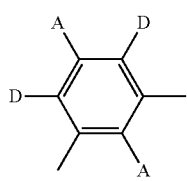
(i-5)
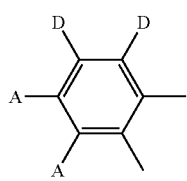
(i-6)
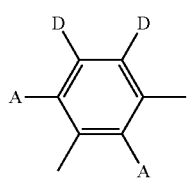
(i-7)
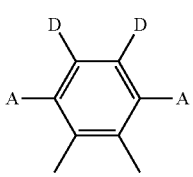
(i-8)
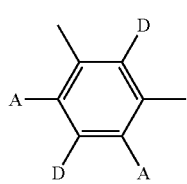
(i-9)
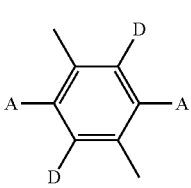
(i-10)
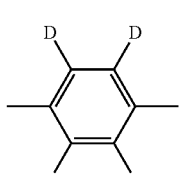
(i-11)
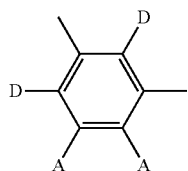
(i-12)
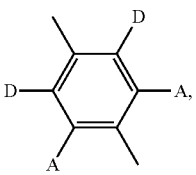
(i-13)
and
wherein D is the electron donor group, and A is the electron acceptor group.
In one embodiment, the electron acceptor group is represented by one of the following structural formulas (A-i-1 to A-i-110):
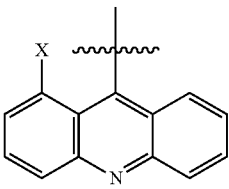
(A-i-1)
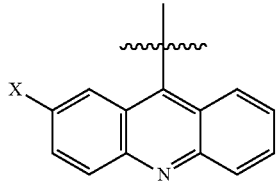
(A-i-2)
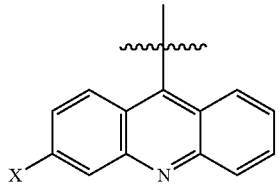
(A-i-3)
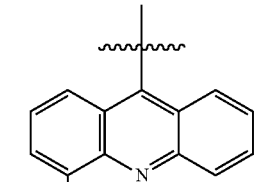
(A-i-4)
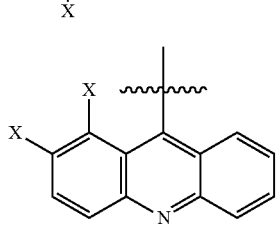
(A-i-5)

-continued
(A-i-6)
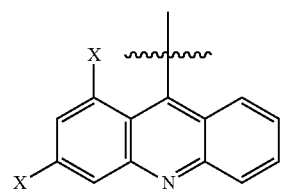
(A-i-7)
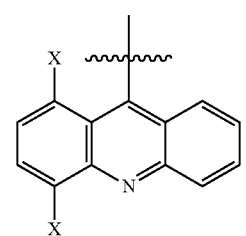
(A-i-8)
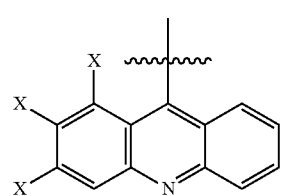
(A-i-9)
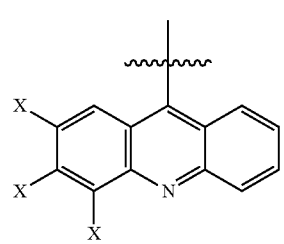
(A-i-10)
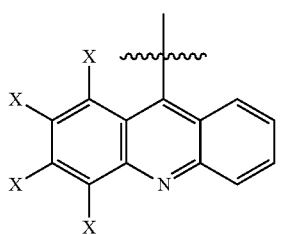
(A-i-11)
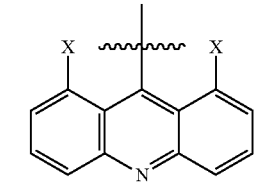
(A-i-12)
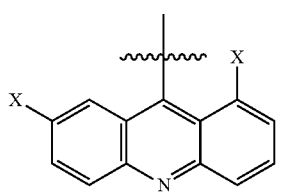
(A-i-13)
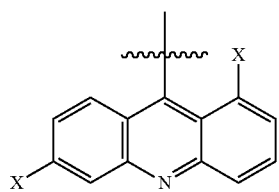
(A-i-14)
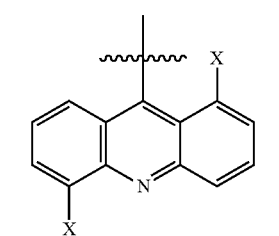
(A-i-15)
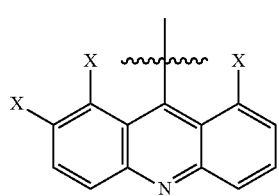
(A-i-16)
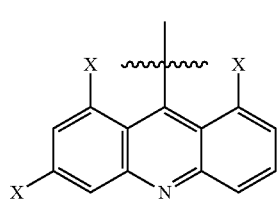
(A-i-17)
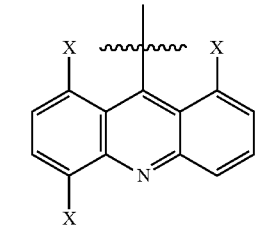
(A-i-18)
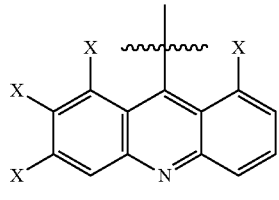
(A-i-19)
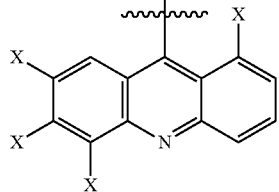

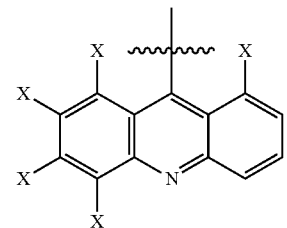
(A-i-20)
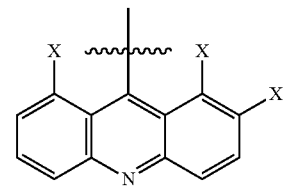
(A-i-21)
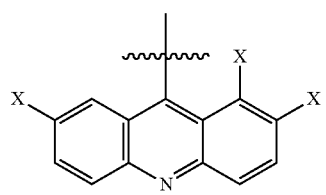
(A-i-22)
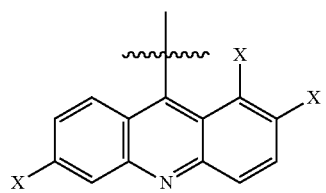
(A-i-23)
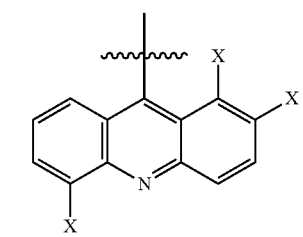
(A-i-24)
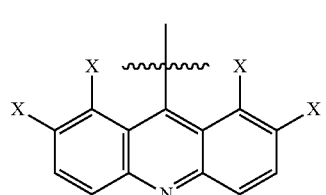
(A-i-25)
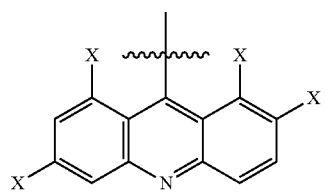
(A-i-26)
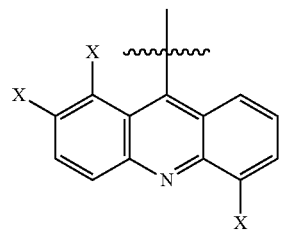
(A-i-27)
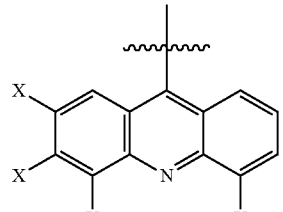
(A-i-28)
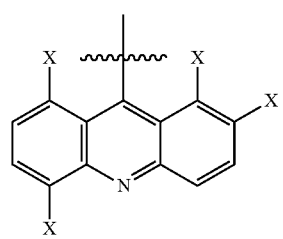
(A-i-29)
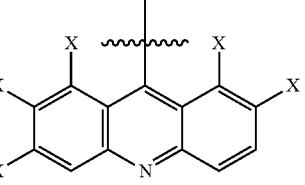
(A-i-30)
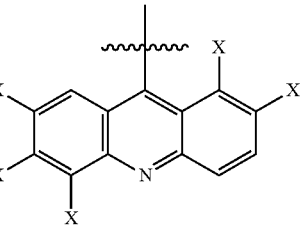
(A-i-31)
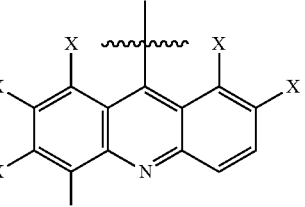
(A-i-32)
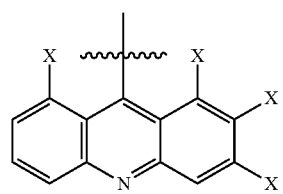
(A-i-33)

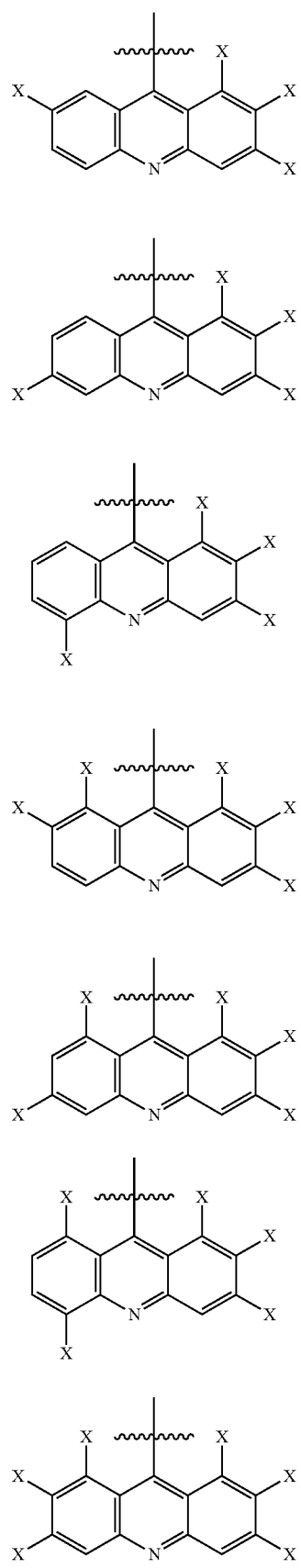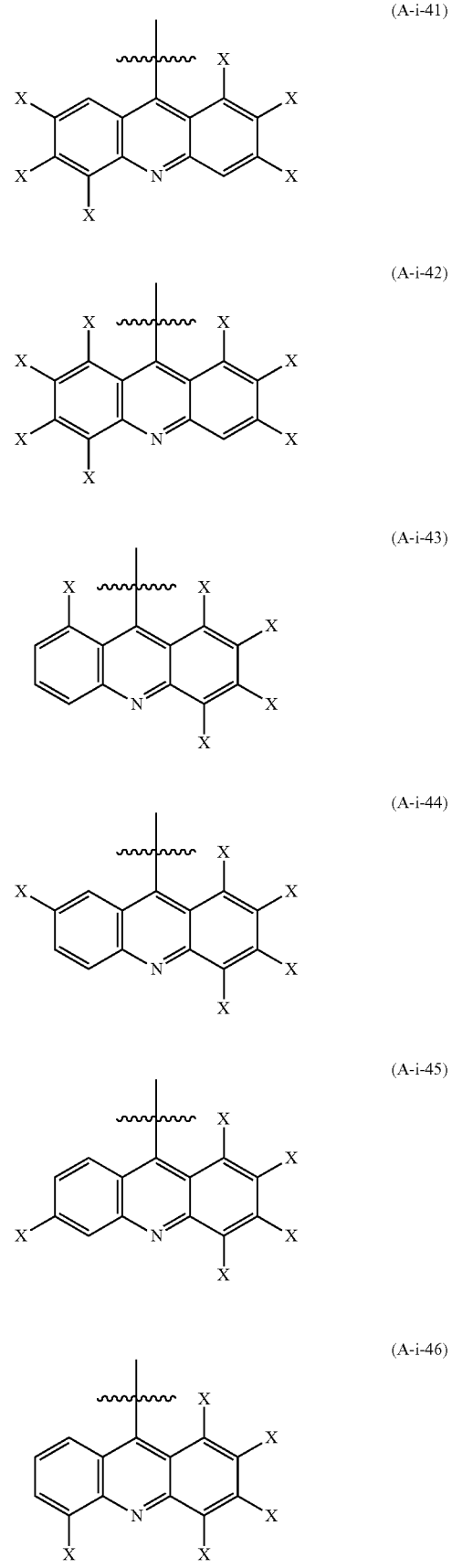

(A-i-47)
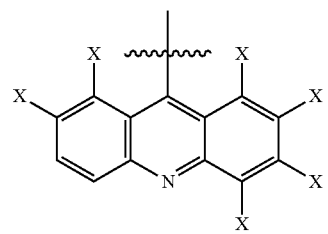
(A-i-48)
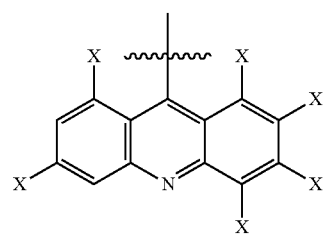
(A-i-49)
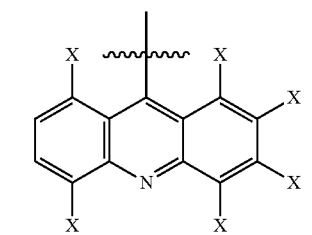
(A-i-50)
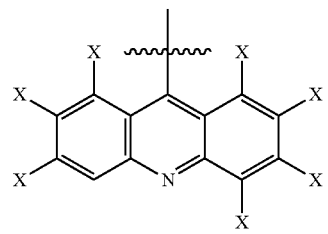
(A-i-51)
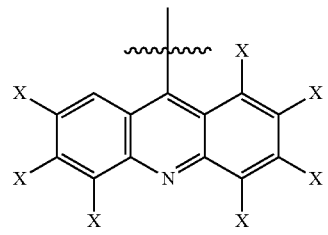
(A-i-52)
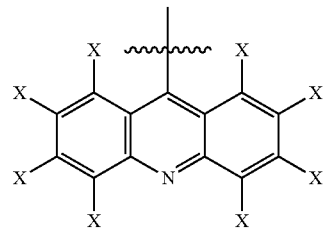
(A-i-53)
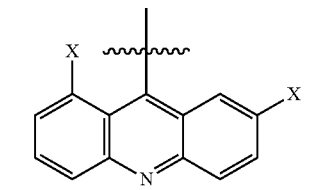
(A-i-54)
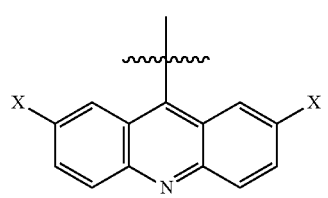
(A-i-55)
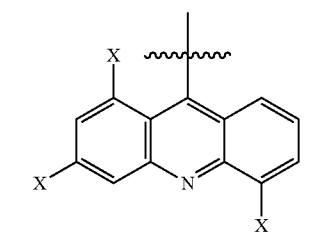
(A-i-56)
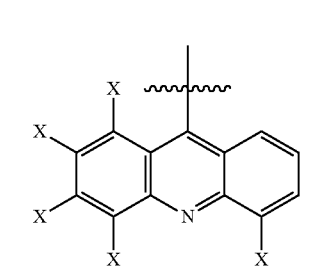
(A-i-57)
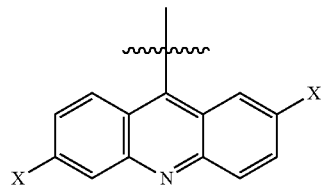
(A-i-58)
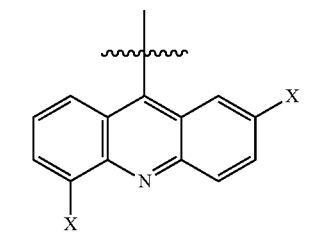
(A-i-59)
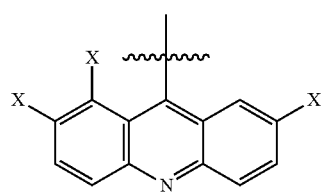
(A-i-60)
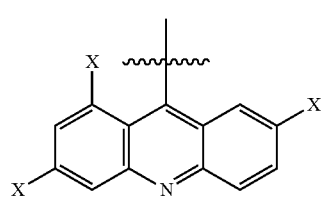

-continued (A-i-61)
(A-i-62)
(A-i-63)
(A-i-64)
(A-i-65)
(A-i-66)
(A-i-67)

-continued (A-i-68)
(A-i-69)
(A-i-70)
(A-i-71)
(A-i-72)
(A-i-73)
(A-i-74)

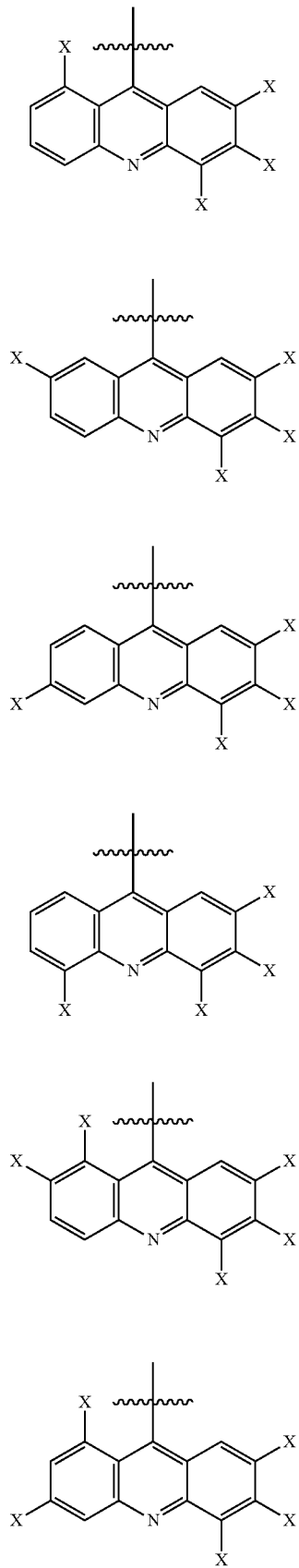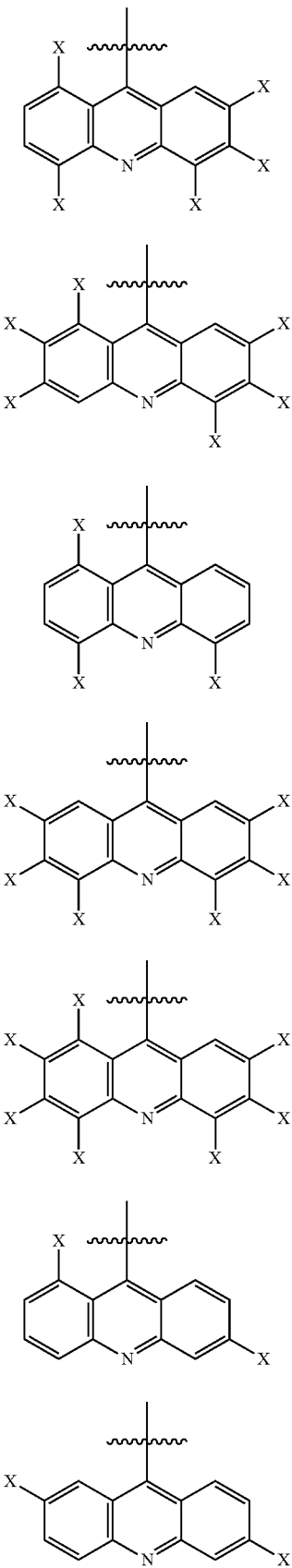

(A-i-88)
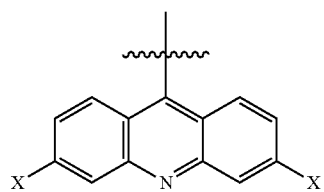
(A-i-89)
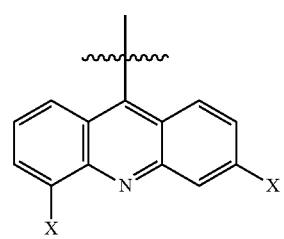
(A-i-90)
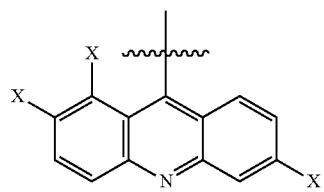
(A-i-91)
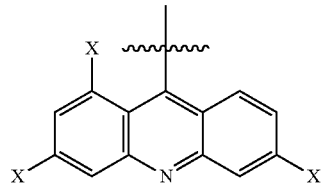
(A-i-92)
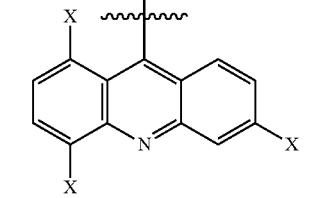
(A-i-93)
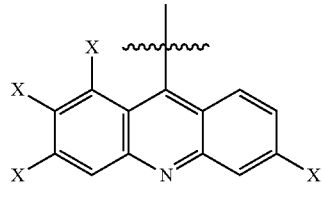
(A-i-94)
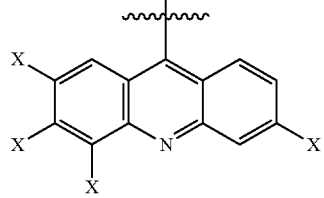
(A-i-95)
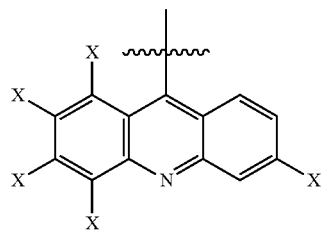
(A-i-96)
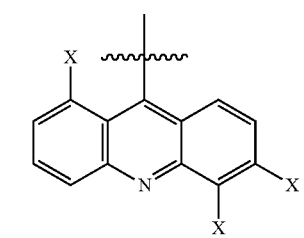
(A-i-97)
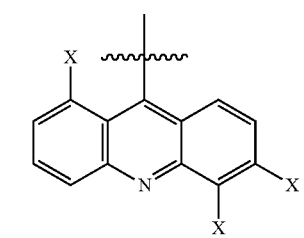
(A-i-98)
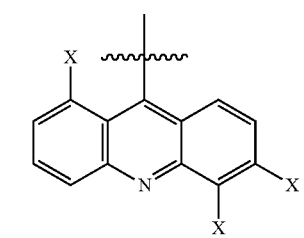
(A-i-99)
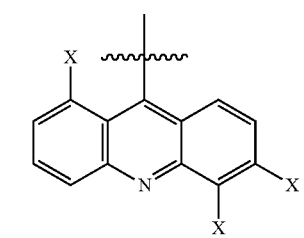
(A-i-100)
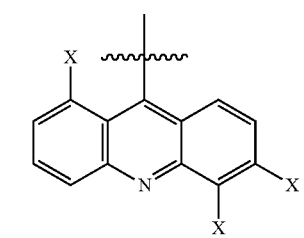

(A-i-101) 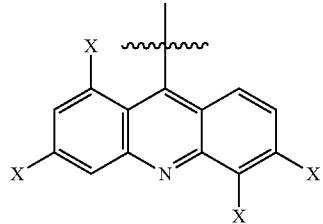
(A-i-102) 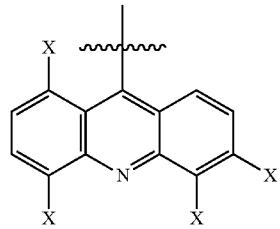
(A-i-103) 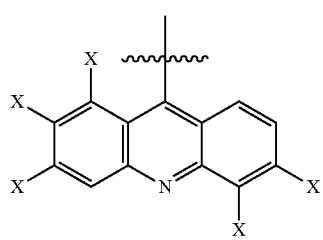
(A-i-104) 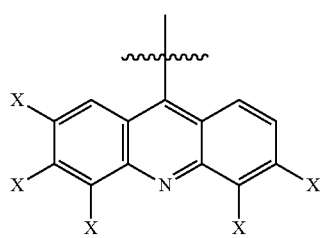
(A-i-105) 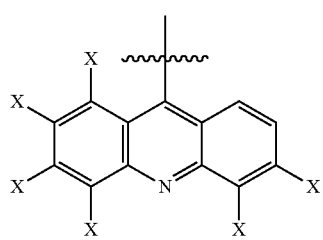
(A-i-106) 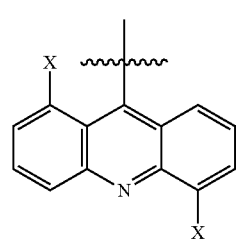
(A-i-107) 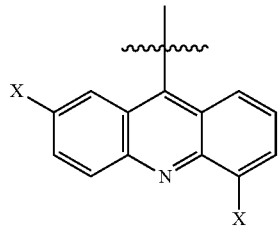
(A-i-108) 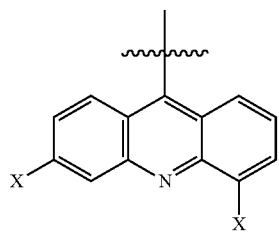
(A-i-109) 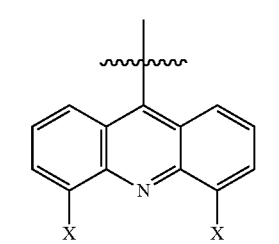
(A-i-110) 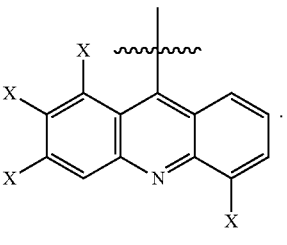
In one preferred embodiment, X is fluorine.
In one preferred embodiment, the electron acceptor is represented by structural formula (A-i-52).
In one preferred embodiment, the TADF material comprises the compound represented by one of the following structural formulas (I-1 to I-3):
(I-1) 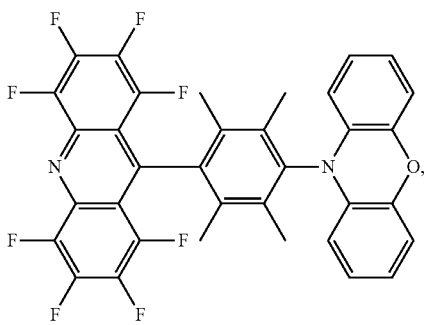

(I-2)

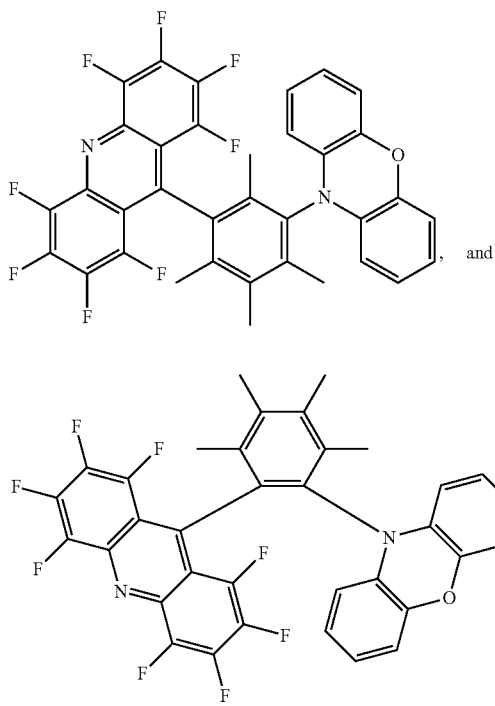

, and (I-3)

According to another aspect of the present invention, an organic electroluminescent (EL) device is provided including a first electrode, a second electrode, and at least one organic EL layer disposed between the first electrode and the second electrode, wherein the organic EL layer includes the above thermally activated delayed fluorescence (TADF) material.

In another embodiment of the present invention, the organic EL layer includes a host material doped with the TADF material.

In one embodiment, a doping concentration of the TADF material is 3% to 5% by weight.

In one embodiment, the host material is 3, 3'-bis(N-carbazoyl)-1,1'-biphenyl.

In one embodiment, the organic EL device further includes a hole injection layer disposed between first electrode and the organic EL layer, a hole transport layer disposed between the hole injection layer and the organic EL layer, and an electron transport layer disposed between the organic EL layer and the second electrode.

In one embodiment, the first electrode is an anode made of indium tin oxide. The second electrode is a cathode made of aluminum or silver-magnesium alloy.

In one embodiment, the hole injection layer is made of molybdenum trioxide, poly(3,4-ethylenedioxythiophene)-polystyrenesulfonic acid (PEDOT:PSS), or polythiophene.

In one embodiment, the hole transport layer is made of an aromatic diamine compound, a triphenylamine compound, or an aromatic triamine compound.

In one embodiment, the electron transport layer is made of 1,3,5-tris(3-(3-pyridyl)phenyl)benzene.

In one embodiment, the electron injection layer is made of lithium fluoride.

According to another aspect of the present invention, a display panel is provided including the above organic electroluminescent (EL) device.

In the present invention, a green light-emitting TADF material having significantly characteristics of TADF material is provided by matching different functional groups. In addition, the present invention provides a reasonable synthesis route to increase synthesis efficiency of the green light-emitting TADF material. The green light-emitting TADF material provided by the present invention can be used in an organic light-emitting layer, thereby realizing a series of high-performance and high-efficiency TADF electronic devices. Furthermore, the green light-emitting TADF material can be applied to a display panel.

BRIEF DESCRIPTION OF THE SEVERAL VIEWS OF THE DRAWINGS

The accompanying figures to be used in the description of embodiments of the present disclosure or prior art will be described in brief to more clearly illustrate the technical solutions of the embodiments or the prior art. Apparently, the accompanying figures described below are only part of the embodiments of the present disclosure, from which figures those skilled in the art can derive further figures without making any inventive efforts.

DESCRIPTION OF SPECIFIC EMBODIMENTS OF THE INVENTION

Figure 1:
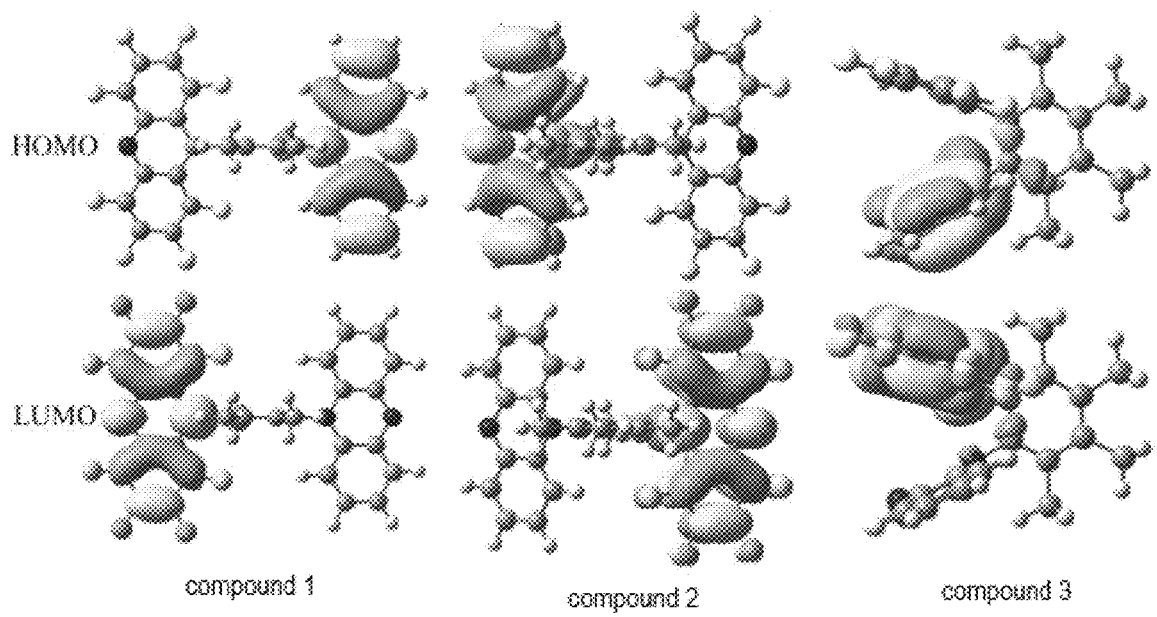
FIG. 1 shows molecular orbital diagrams of compounds 1 to 3 according to a first embodiment, a second embodiment, and a third embodiment of the present invention.

The embodiments of the present disclosure are described in detail hereinafter. Examples of the described embodiments are given in the accompanying drawings, wherein the identical or similar reference numerals constantly denote the identical or similar elements or elements having the identical or similar functions. The specific embodiments described with reference to the attached drawings are all exemplary and are intended to illustrate and interpret the present disclosure, which shall not be construed as causing limitations to the present disclosure.

In the description of the present disclosure, unless specified or limited otherwise, it should be noted that, a structure in which a first feature is "on" or "beneath" a second feature may include an embodiment in which the first feature directly contacts the second feature and may also include an embodiment in which an additional feature is formed between the first feature and the second feature so that the first feature does not directly contact the second feature. Furthermore, a first feature "on," "above," or "on top of" a second feature may include an embodiment in which the first feature is right "on," "above," or "on top of" the second feature and may also include an embodiment in which the first feature is not right "on," "above," or "on top of" the second feature, or just means that the first feature has a sea level elevation greater than the sea level elevation of the second feature. While first feature "beneath," "below," or "on bottom of" a second feature may include an embodiment in which the first feature is right "beneath," "below," or "on bottom of" the second feature and may also include an embodiment in which the first feature is not right "beneath," "below," or "on bottom of" the second feature, or just means that the first feature has a sea level elevation less than the sea level elevation of the second feature.

The disclosure herein provides many different embodiments or examples for realizing different structures of the present disclosure. In order to simplify the disclosure of the present disclosure, components and settings of specific examples are described below. Of course, they are only examples and are not intended to limit the present disclosure. Furthermore, reference numbers and/or letters may be repeated in different examples of the present disclosure. Such repetitions are for simplification and clearness, which per se do not indicate the relations of the discussed embodiments and/or settings. Moreover, the present disclosure provides examples of various specific processes and materials, but the applicability of other processes and/or application of other materials may be appreciated by a person skilled in the art.

First Embodiment: Specific Structure of Compound Represented by Formula (1)

In the present embodiment, specific structure of compound represented by formula (1) is described by table (1). A thermally activated delayed fluorescence (TADF) material provided by the present invention includes a compound represented by the following structural formula (1):

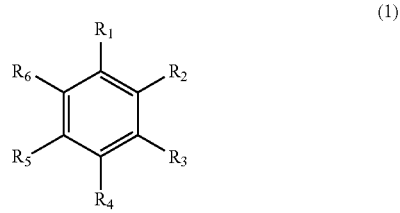

(1)

Table 1

| numerals | structural formula |
| --- | --- |
| 1 | (benzene ring with D top, A bottom) |
| 2 | (benzene ring with A left, D top) |
| 3 | (benzene ring with A and D on top) |
| 4 | (benzene ring with A, D top, D left, A bottom) |
| 5 | (benzene ring with A, D top, D left, A right) |
| 6 | (benzene ring with D, D top, A left, A bottom) |
| 7 | (benzene ring with D, D top, A left, A right) |
| 8 | (benzene ring with D, D top, A left, A right) |
| 9 | (benzene ring with D top, A left, D and A bottom) |
| 10 | (benzene ring with D top, A left, A right, D bottom) |
| 11 | (benzene ring with D, D top, A, A bottom) |

Table 1-continued

| numerals | structural formula |
|---|---|
| 12 | ![structure 12 with D, D, A, A substituents] |
| 13 | ![structure 13 with D, D, A, A substituents] | wherein D is an electron donor group represented by the following formula (D-i), and A is an electron acceptor group represented by the following structural formula (A-i-52):

(D-i)

(A-i-52)

and
wherein X is fluorine.

Second Embodiment: A Manufacturing Process of Compound 1

In the present embodiment, a TADF material is provided including compound 1 represented by the following structural formula (I-1):

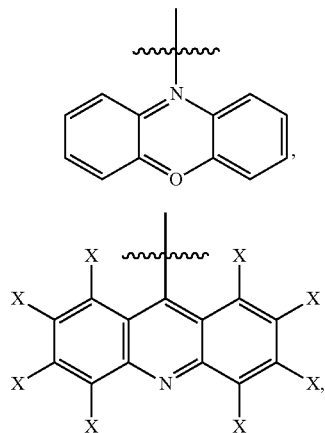

(I-1)

Synthesis of compound 1 is illustrated bellow:

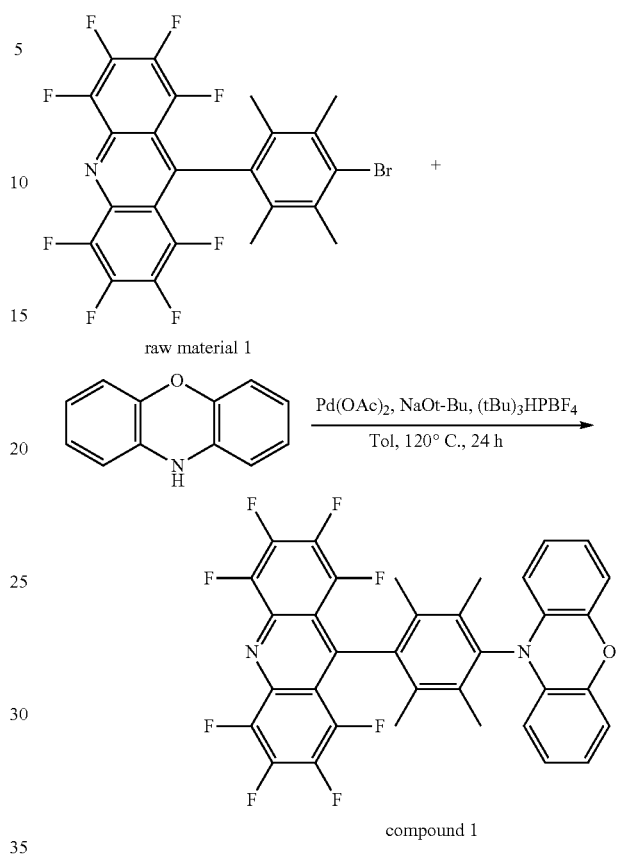

Specific synthesizing process is illustrated below:

step 1: Adding raw material 1 (2.67 g, 5 mmol), phenoxazine (1.1 g, 6 mmol), palladium acetate (45 mg, 0.2 mmol), and tri-tert-butylphosphine tetrafluoroborate (0.17 g, 0.6 mmol) into a two-neck bottle. Then, placing the two-neck bottle in a closed environment and adding NaOt-Bu (0.58 g, 6 mmol) into the two-neck bottle. Then, adding water- and oxygen-free toluene (40 ml) into the two-neck bottle in argon environment at 120 degrees Celsius for 24 hours to form a reacting solution.

step 2: adding the reacting solution into cold water after the reacting solution reaches to room temperature. Extracting organic phase from the reacting solution for three times by dichloromethane. Combining the organic phase extracted from the reacting solution, and purifying the combined organic phase by silica gel column chromatography (volume ratio of dichloromethane to hexane is 3:2) to obtain a green powder (2.0 g, yield 63%). CH NMR (300 MHz, $CD_2Cl_2$, δ): 7.14 (d, J=6.6 Hz, 2H), 7.01-6.96 (m, 6H), 2.60 (s, 6H), 2.12 (s, 6H). MS (EI) m/z: $[M]^+$ calcd for $C_{35}H_{20}F_8N_2O$, 636.14; found, 636.09)

Third Embodiment: A Manufacturing Process of Compound 2

In the present embodiment, a TADF material is provided including compound 2 represented by the following structural formula (I-2):

(I-2)

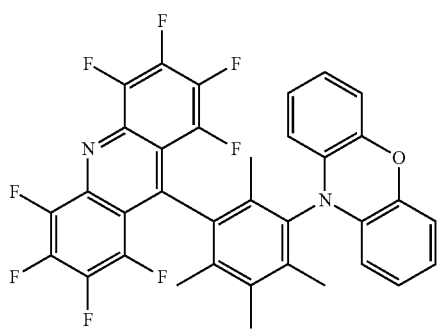

Synthesis of compound 2 is illustrated bellow:

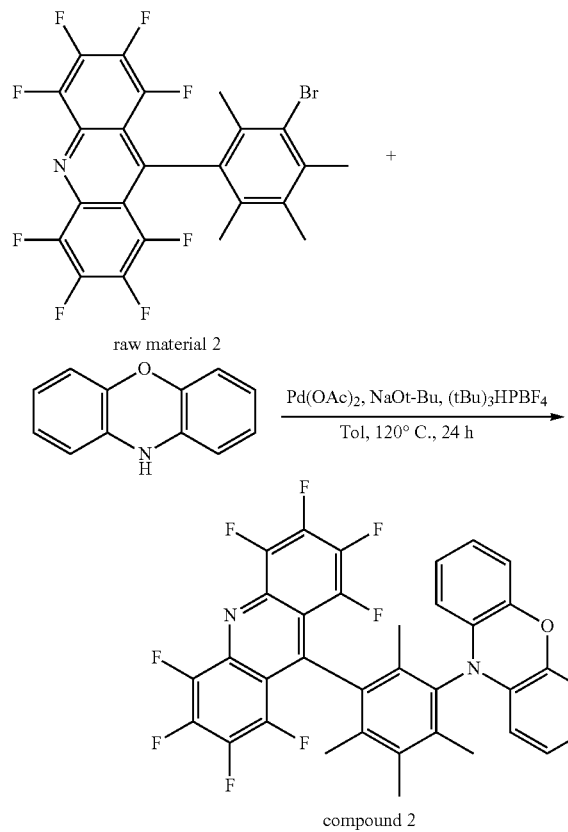

Specific synthesizing process is illustrated below:
step 1: Adding raw material 2 (2.67 g, 5 mmol), phenoxazine (1.1 g, 6 mmol), palladium acetate (45 mg, 0.2 mmol), and tri-tert-butylphosphine tetrafluoroborate (0.17 g, 0.6 mmol) into a 100 ml two-neck bottle. Then, placing the two-neck bottle in a closed environment and adding NaOt-Bu (0.58 g, 6 mmol) into the two-neck bottle. Then, adding water- and oxygen-free toluene (40 ml) into the two-neck bottle in argon environment at 120 degrees Celsius for 24 hours to form a reacting solution.
step 2: adding the reacting solution into cold water (200 ml) after the reacting solution reaches to room temperature. Extracting organic phase from the reacting solution for three times by dichloromethane. Combining the organic phase extracted from the reacting solution, and purifying the combined organic phase by silica gel column chromatography (volume ratio of dichloromethane to hexane is 3:2) to obtain a green powder (1.6 g, yield 50%). ($^1$H NMR (300 MHz, CD$_2$Cl$_2$, δ): 7.14 (d, J=6.6 Hz, 2H), 7.01-6.96 (m, 6H), 2.60 (s, 3H), 2.25 (s, 3H), 2.18 (s, 3H), 2.12 (s, 3H). MS (EI) m/z [M]$^+$ calcd for C$_{35}$H$_{20}$F$_8$N$_2$O, 636.14; found, 636.12)

Fourth Embodiment: A Manufacturing Process of Compound 3

In the present embodiment, a TADF material is provided including compound 3 represented by the following structural formula (I-3):

(I-3)

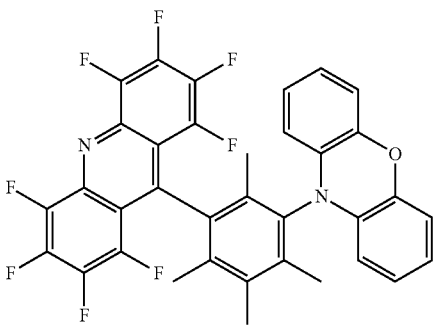

Synthesis of compound 3 is illustrated bellow:

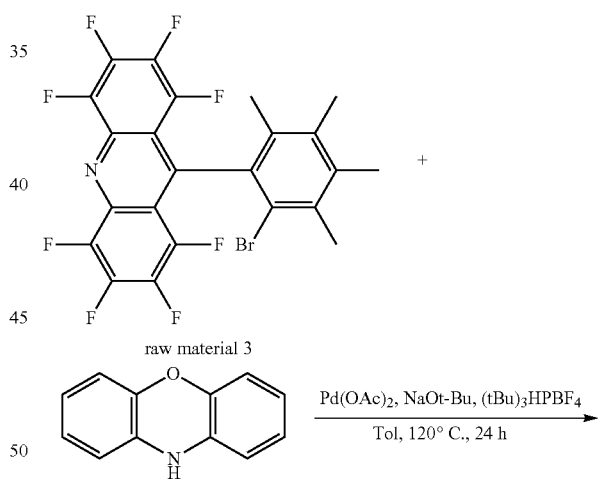

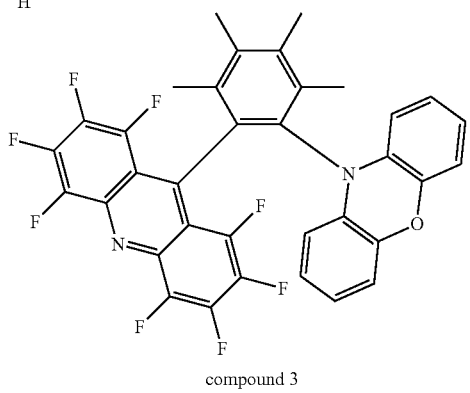

Specific synthesizing process is illustrated below:

step 1: Adding raw material 3 (2.67 g, 5 mmol), phenoxazine (1.1 g, 6 mmol), palladium acetate (45 mg, 0.2 mmol), and tri-tert-butylphosphine tetrafluoroborate (0.17 g, 0.6 mmol) into a 100 ml two-neck bottle. Then, placing the two-neck bottle in a closed environment and adding NaOt-Bu (0.58 g, 6 mmol) into the two-neck bottle. Then, adding water- and oxygen-free toluene (40 ml) into the two-neck bottle in argon environment at 120 degrees Celsius for 24 hours to form a reacting solution.

step 2: adding the reacting solution into cold water (200 ml) after the reacting solution reaches to room temperature. Extracting organic phase from the reacting solution for three times by dichloromethane. Combining the organic phase extracted from the reacting solution, and purifying the combined organic phase by silica gel column chromatography (volume ratio of dichloromethane to hexane is 3:2) to obtain a green powder (1.0 g, yield 33%). ($^1$H NMR (300 MHz, CD$_2$Cl$_2$, δ): 7.14 (d, J=6.6 Hz, 2H), 7.01-6.96 (m, 6H), 2.60 (s, 3H), 2.18 (s, 6H), 2.12 (s, 3H). MS (EI) m/z: [M]$^+$ calcd for C$_{35}$H$_{20}$F$_8$N$_2$O, 636.14; found, 636.12)

Fifth Embodiment: Experimental Verification and Detection of the Compounds 1 to 3

In the present embodiment, experimental verification and detection of the compounds 1 to 3 are illustrated below:

Referring to FIG. 1, FIG. 1 shows molecular orbital diagrams of the compounds 1 to 3, which shows electron cloud distribution of highest occupied molecular orbital (HOMO) and lowest unoccupied molecular orbital (LUMO) of the compounds 1 to 3.

Energy of the lowest singlet state (s1), energy of the lowest triplet state (t1), and electrochemical data of the compounds 1 to 3 shown in table 2 were obtained by theoretical simulation:

TABLE 2

|  | PL Peak (nm) | S$_1$ (eV) | T$_1$ (eV) | □E$_{ST}$ (eV) | HOMO (eV) | LUMO (eV) |
| --- | --- | --- | --- | --- | --- | --- |
| compound 1 | 513 | 2.42 | 2.33 | 0.09 | −5.52 | −2.43 |
| compound 2 | 526 | 2.36 | 2.29 | 0.07 | −5.63 | −2.44 |
| compound 3 | 528 | 2.35 | 2.29 | 0.06 | −5.66 | −2.43 |

Figure 2:
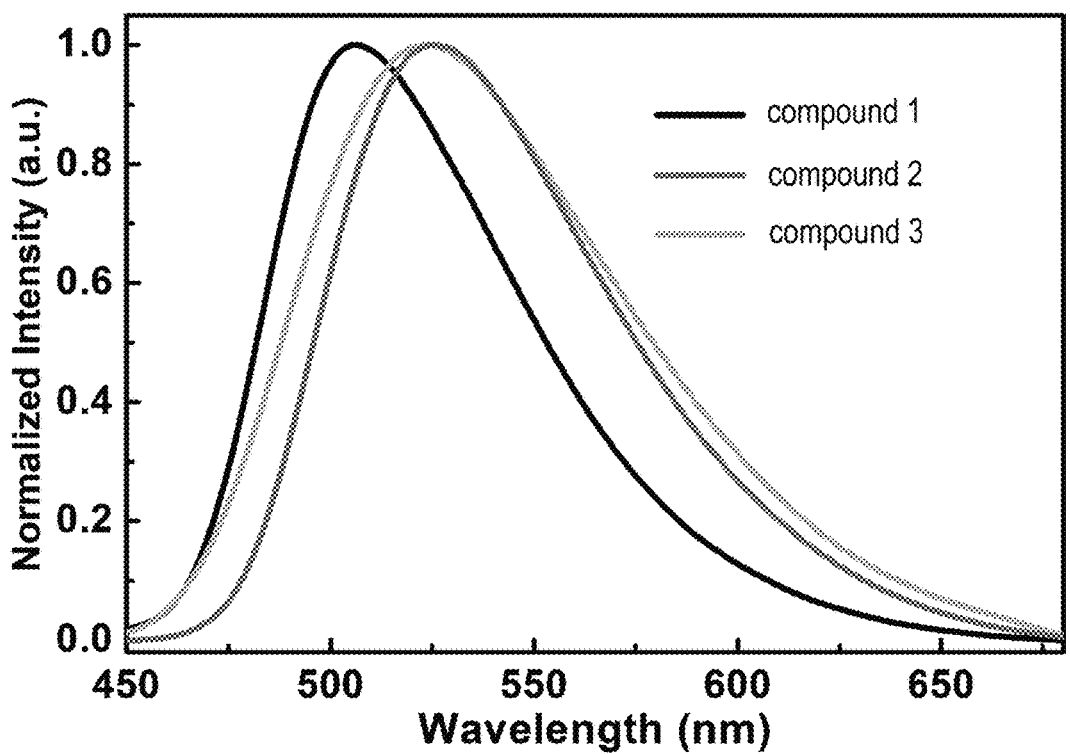
FIG. 2 shows spectra of compounds 1 to 3 in toluene solution at room temperature.

In addition, in the present embodiment, photophysical properties of the compounds 1 to 3 are examined to obtain FIG. 2. FIG. 2 shows spectra of compounds 1 to 3 in toluene solution at room temperature.

According to the above experimental data, compounds 1 to 3 have relatively small energy gap between the lowest singlet and triplet excited states ($\Delta E_{ST}$), and are suitable for being applied to organic light-emitting diodes (OLEDs) as green light-emitting TADF materials.

Sixth Embodiment: An Organic Light-Emitting Device

Figure 3:
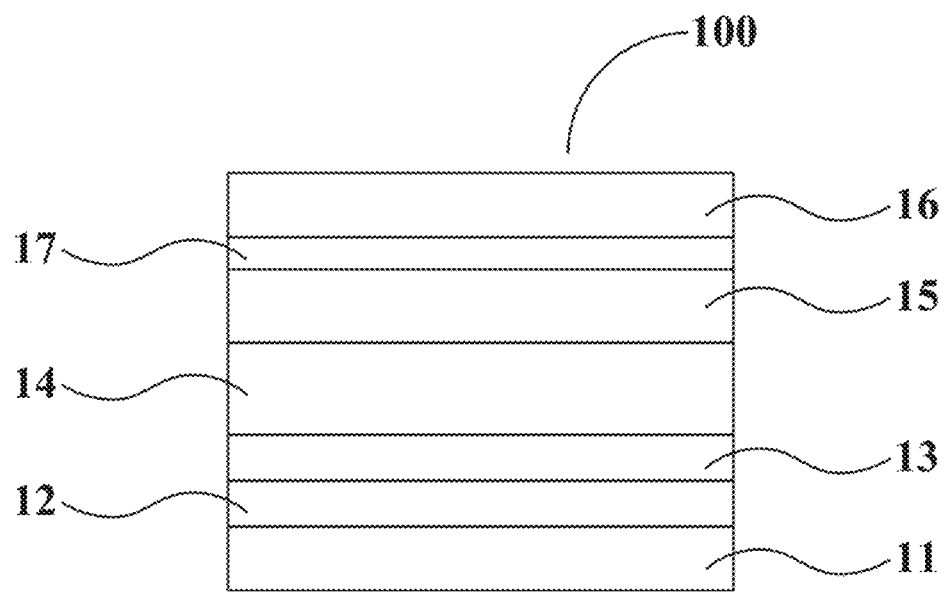
FIG. 3 is a schematic diagram showing a structure of an organic light-emitting device according to an embodiment of the present invention.

In the present embodiment, an organic light-emitting device is provided. As shown in FIG. 3, an organic light-emitting device 100 includes a first electrode 11, a hole injection layer 12, a hole transport layer 13, an organic light-emitting layer 14, an electron transport layer 15, and a second electrode 16 which are sequentially disposed on each other. The organic light-emitting layer 14 includes a green light-emitting TADF material. The green light-emitting TADF material includes at least one of the compound 1, the compound 2, and the compound 3 according to embodiments 2 to 4.

It should be noted that the organic light-emitting device 100 shown in FIG. 3 is merely an example, functional layers of the organic light-emitting device 100 can be added or removed by those skilled in the art according to the practical situation. For instance, an electron injection layer 17 can be disposed between the electron transport layer 15 and the second electrode 16. Furthermore, the above layers are formed by a normal process and are made of a normal material.

For instance, the first electrode 11 is an anode which can be made of indium tin oxide (ITO).

For instance, the hole injection layer 12 can be made of MoO$_3$, poly(3,4-ethylenedioxythiophene):poly(styrene sulfonate) (PEDOT:PSS), or polythiophene.

For instance, the hole transport layer 13 can be made of aromatic diamines, triphenylamine compound, or aromatic triamines. The hole transport layer 13 can be made of tris(4-carbazoyl-9-ylphenyl)amine (TCTA), for example.

For instance, the organic light-emitting layer 14 includes a host material, 3,3-Di(9H-carbazol-9-yl)biphenyl (MCBP), doped with at least one of the compound 1, the compound 2, and the compound 3. A doping concentration of the compounds 1 to 3 is but no limited to 3%.

For instance, the electron transport layer 15 can be made of 1,3,5-Tris(3-pyridyl-3-phenyl)benzene (TmPyPB).

For instance, the second electrode 16 is cathode which can be made of Al or Mg/Ag.

For instance, the electron injection layer 17 can be made of LiF.

For instance, a method of manufacturing the organic light-emitting device 100 includes a plurality of steps of: spin coating PESOT:PSS on a cleaned ITO substrate, and then sequentially evaporating TmPyPB, LiF, and Al on the cleaned ITO substrate.

In the present embodiment, the organic light-emitting layer 14 including the compound 1 is denoted with device A, the organic light-emitting layer 14 including the compound 2 is denoted with device B, and the organic light-emitting layer 14 including the compound 3 is denoted with device C.

In the present embodiment, specific structures of the device A, device B, and device C are described as follows:

device A: ITO/MoO3(2 nm)/TCTA(35 nm)/MCBP: compound 1 (3% 40 nm)/TmPyPB(40 nm)/LiF(1 nm)/Al(100 nm), device B: ITO/MoO3(2 nm)/TCTA(35 nm)/MCBP: compound 2(3% 40 nm)/TmPyPB(40 nm)/LiF(1 nm)/Al(100 nm), device C: ITO/MoO3(2 nm)/TCTA(35 nm)/mCBP: compound 3 (3% 40 nm)/TmPyPB(40 nm)/LiF(1 nm)/Al(100 nm).

The highest current efficiency, CIEx color gamut, and the highest external quantum efficiency (EQE) of the device A, the device, B, and device C are examined by a calibrated silicon photodiode (Keithley 2400 Sourcemeter, Keithley 2000 Currentmeter), and data is shown in table 3. Moreover, spectra of device A, device B, and device C are obtained by a spectrometer (SPEX CCD3000) made by French JY company.

TABLE 3

| numerals | the highest current efficiency (cd/A) | CIEx color gamut | the highest EQE(%) |
|---|---|---|---|
| device A | 134.5 | 0.22 | 35.7 |
| device B | 124.3 | 0.23 | 31.8 |
| device C | 112.5 | 0.23 | 28.9 |

The above data shows that light emitted by the device A, the device B, and the device C is green.

Seventh Embodiment: A Display Panel

Figure 4:
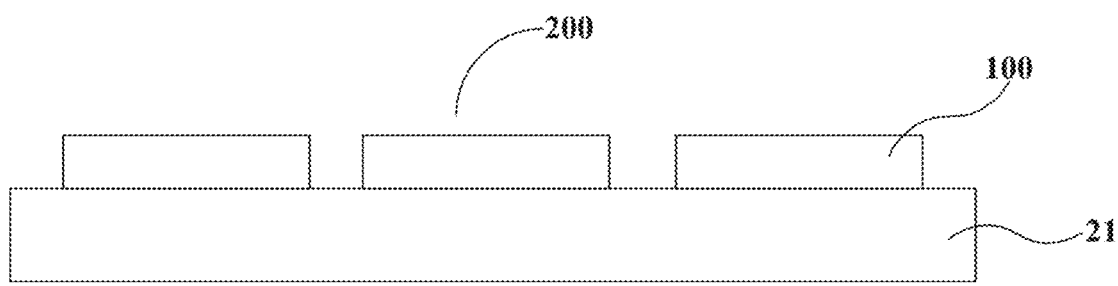
FIG. 4 is a schematic diagram showing a structure of a display panel according to an embodiment of the present invention.

In the present embodiment, a display panel is provided. As shown in FIG. 4, a display panel 200 includes a substrate 21, wherein the plurality of organic light-emitting devices 100 are formed on the substrate 21. The organic light-emitting devices 100 can be the device A, the device B, or the device C. It should be noted, other structures such as non-organic film layers, a thin film transistor, layers of the thin film transistor, and wires. Furthermore, the display panel 200 further includes normal structures like an encapsulating plate, while other normal structures will not be described here.

In the present invention, a green light-emitting TADF material having significantly characteristics of TADF material is provided by matching different functional groups. In addition, the present invention provides a reasonable synthesis route to increase synthesis efficiency of the green light-emitting TADF material. The green light-emitting TADF material provided by the present invention can be used in an organic light-emitting layer, thereby realizing a series of high-performance and high-efficiency TADF electronic devices. Furthermore, the green light-emitting TADF material can be applied to a display panel.

The present disclosure has been described with a preferred embodiment thereof. The preferred embodiment is not intended to limit the present disclosure, and it is understood that many changes and modifications to the described embodiment can be carried out without departing from the scope and the spirit of the disclosure that is intended to be limited only by the appended claims.

The present invention can be manufactured and used in the industry, so it possesses industrial practicability.

What is claimed is:

1. A thermally activated delayed fluorescence (TADF) material, comprising a compound represented by the following structural formula (1):

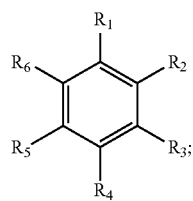

(1)

wherein $R_1$ to $R_6$ each independently represents a methyl group, an electron acceptor group represented by the following structural formula (A-i), or an electron donor group;

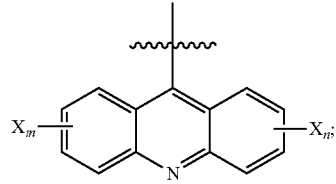

(A-i)

wherein X is a halogen atom, and m and n each independently represents an integer from 1 to 4;

wherein the electron donor group is a substituted or unsubstituted phenoxazinyl group; and wherein the compound comprises at least one electron acceptor group and at least one electron donor group.

2. The TADF material of claim 1, wherein the TADF material comprises the compound represented by one of the following structural formulas (i-1 to i-13):

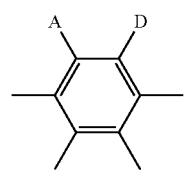

(i-1)

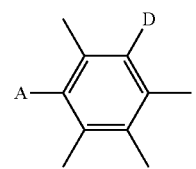

(i-2)

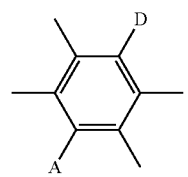

(i-3)

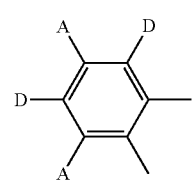

(i-4)

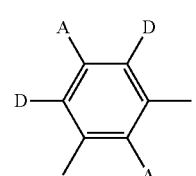

(i-5)

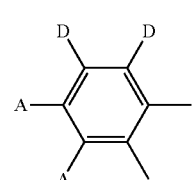

(i-6)

-continued
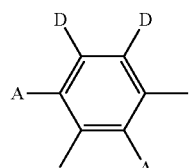
(i-7)
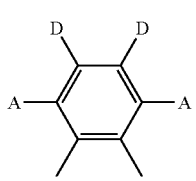
(i-8)
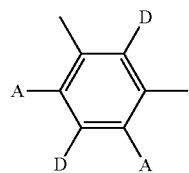
(i-9)
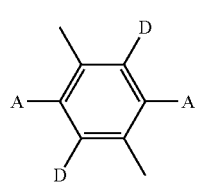
(i-10)
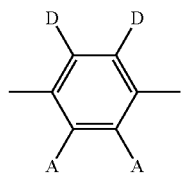
(i-11)
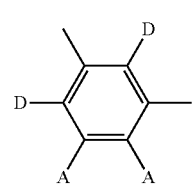
(i-12)
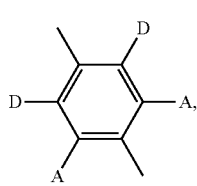
(i-13)
and
wherein D is the electron donor group, and A is the electron acceptor group.
3. The TADF material of claim 2, wherein the electron acceptor group is represented by one of the following structural formulas (A-i-1 to A-i-110):
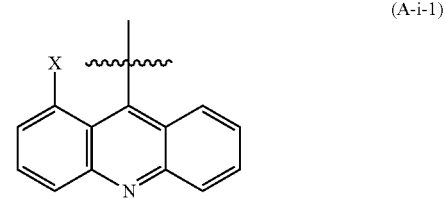
(A-i-1)
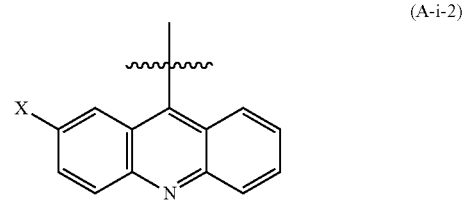
(A-i-2)
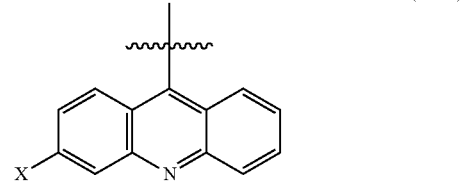
(A-i-3)
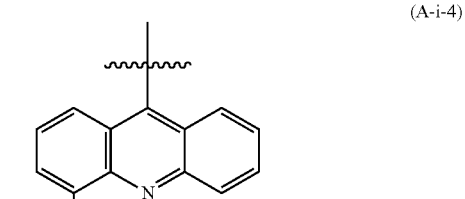
(A-i-4)
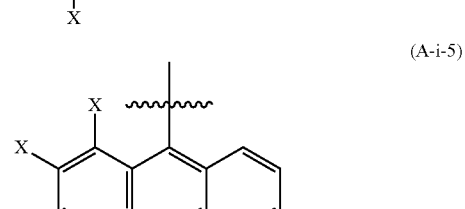
(A-i-5)
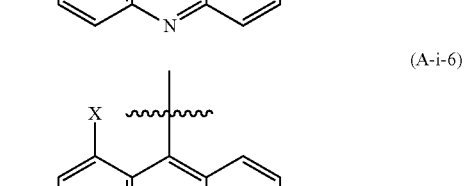
(A-i-6)
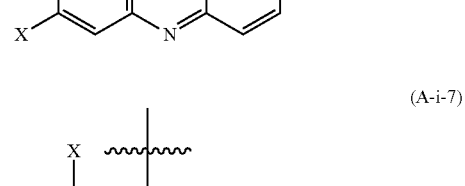
(A-i-7)

(A-i-8)
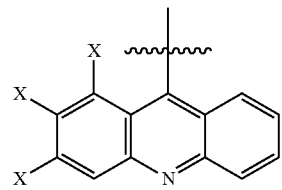
(A-i-9)
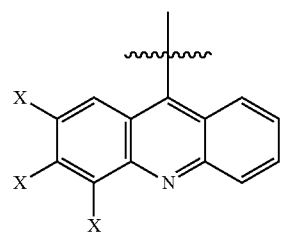
(A-i-10)
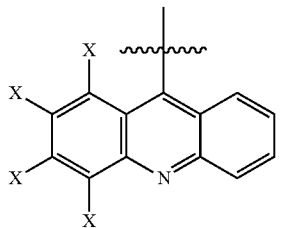
(A-i-11)
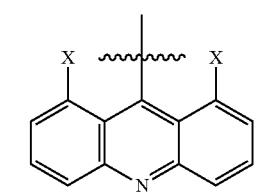
(A-i-12)
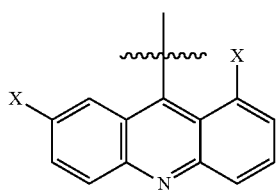
(A-i-13)
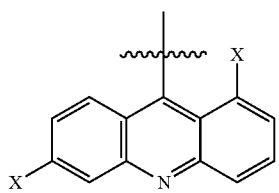
(A-i-14)
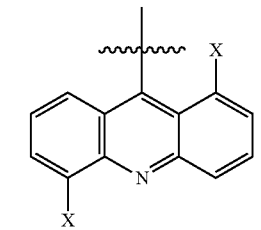
(A-i-15)
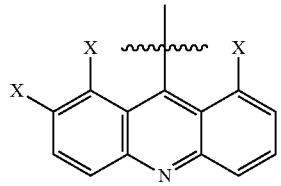
(A-i-16)
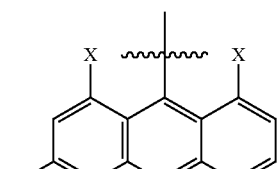
(A-i-17)
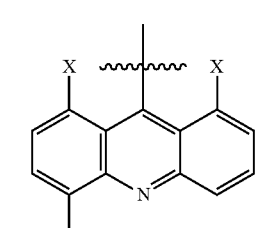
(A-i-18)
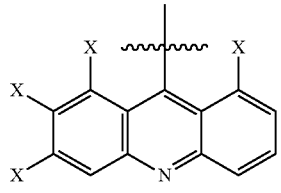
(A-i-19)
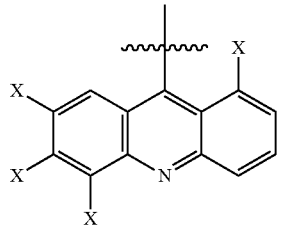
(A-i-20)
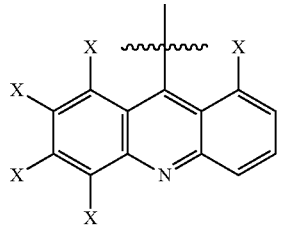
(A-i-21)
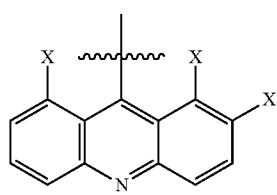

-continued
(A-i-22)
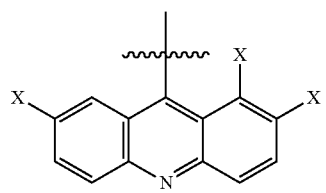
(A-i-23)
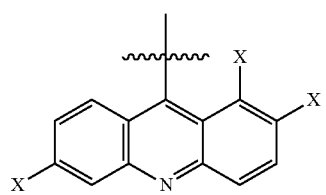
(A-i-24)
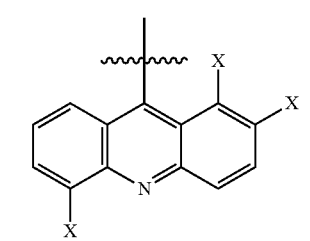
(A-i-25)
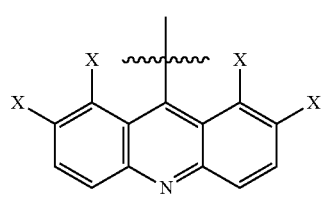
(A-i-26)
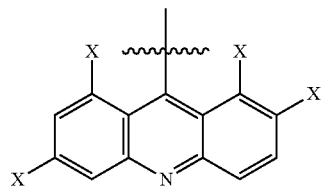
(A-i-27)
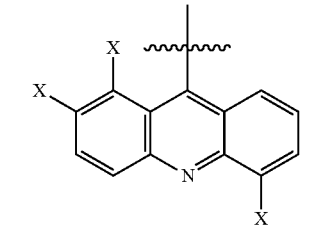
(A-i-28)
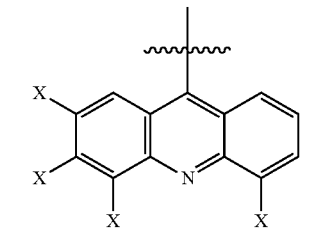
-continued
(A-i-29)
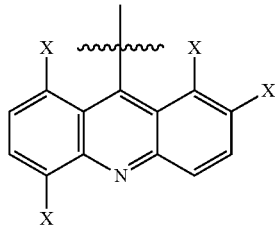
(A-i-30)
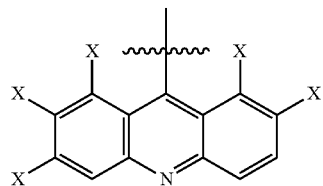
(A-i-31)
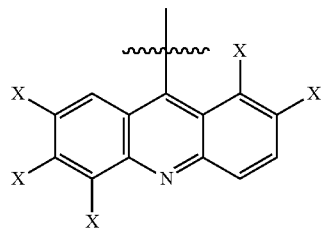
(A-i-32)
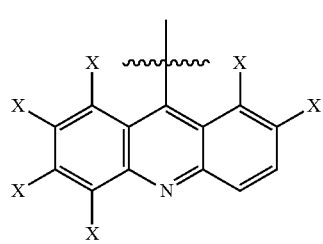
(A-i-33)
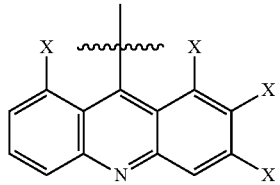
(A-i-34)
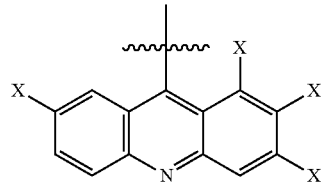
(A-i-35)
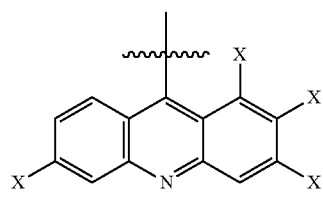

-continued
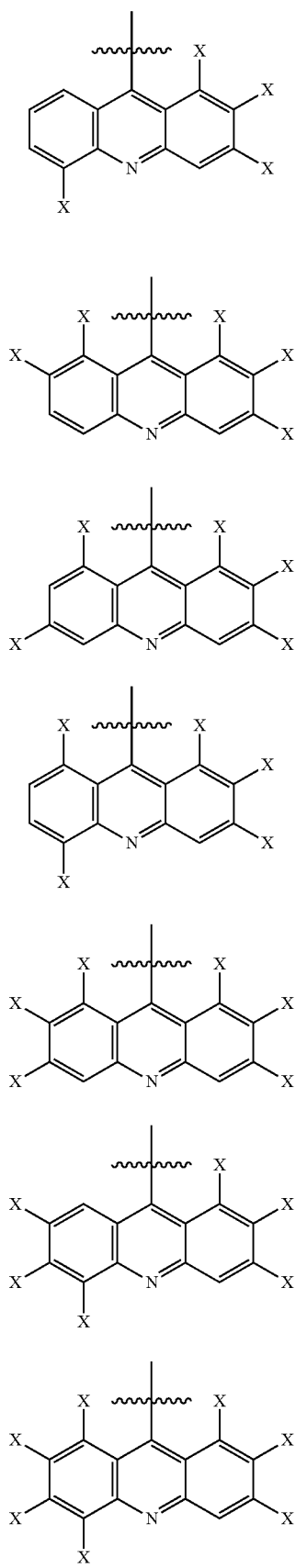
(A-i-36)
(A-i-37)
(A-i-38)
(A-i-39)
(A-i-40)
(A-i-41)
(A-i-42)
-continued
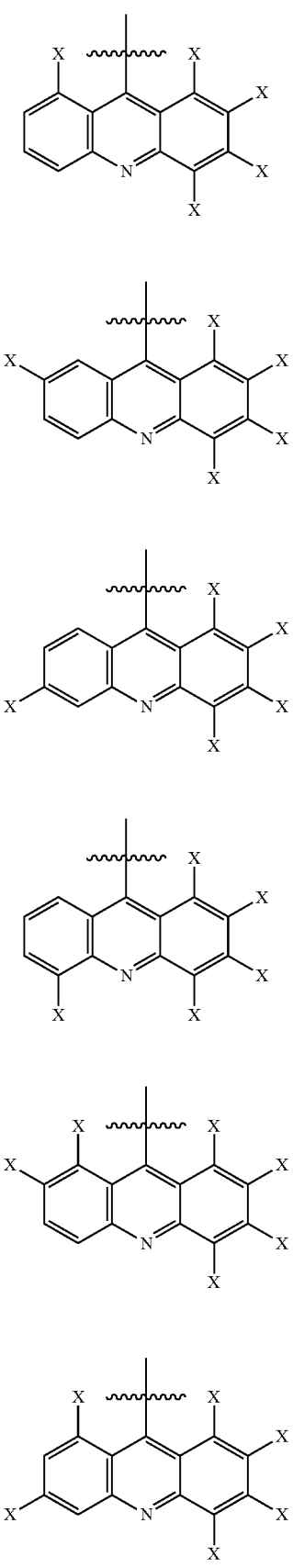
(A-i-43)
(A-i-44)
(A-i-45)
(A-i-46)
(A-i-47)
(A-i-48)

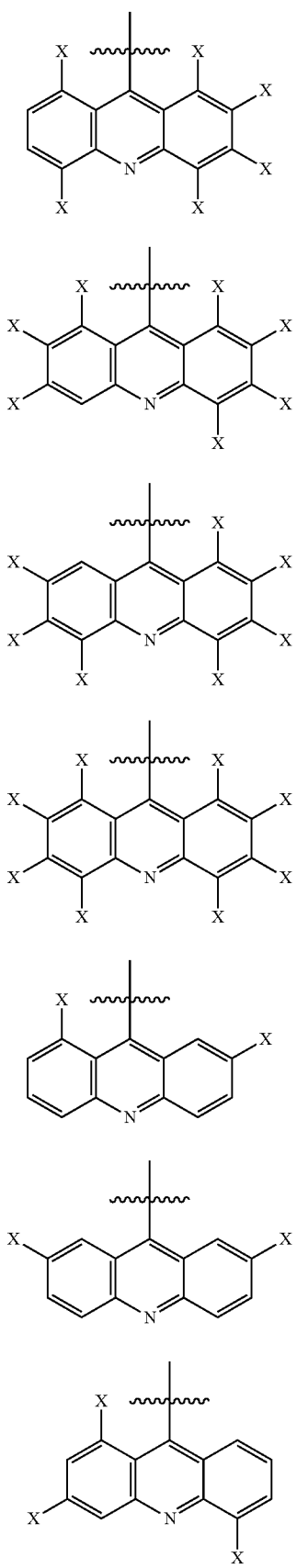
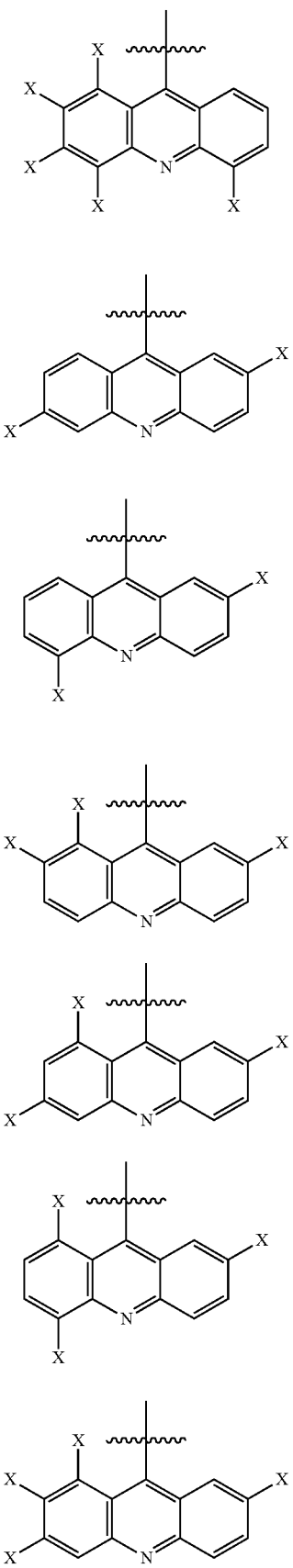

(A-i-63)
(A-i-64)
(A-i-65)
(A-i-66)
(A-i-67)
(A-i-68)
(A-i-69)
(A-i-70)
(A-i-71)
(A-i-72)
(A-i-73)
(A-i-74)
(A-i-75)
(A-i-76)

(A-i-77)
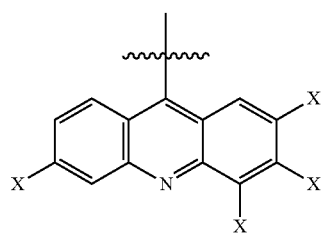
(A-i-78)
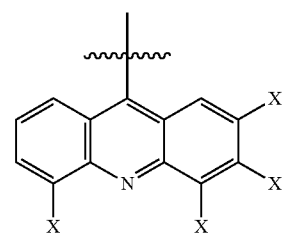
(A-i-79)
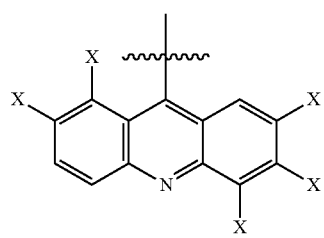
(A-i-80)
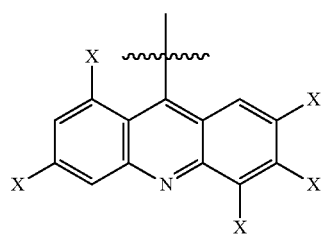
(A-i-81)
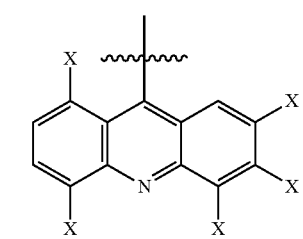
(A-i-82)
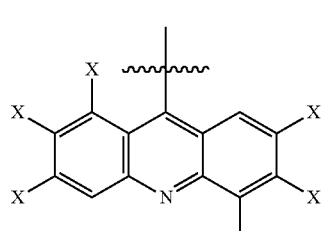
(A-i-83)
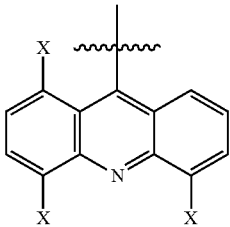
(A-i-84)
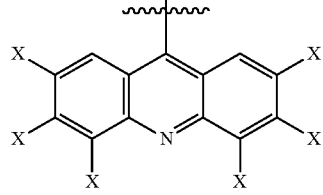
(A-i-85)
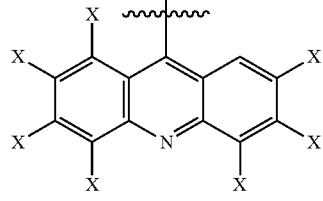
(A-i-86)
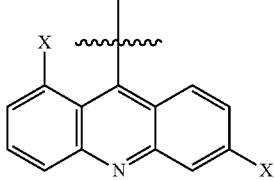
(A-i-87)
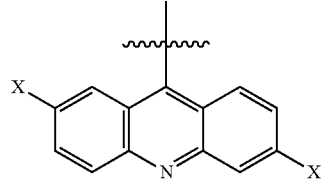
(A-i-88)
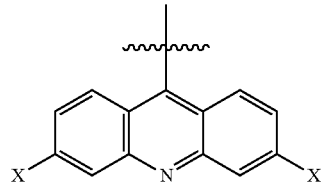
(A-i-89)
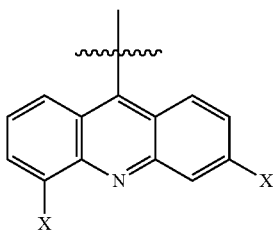

(A-i-90) 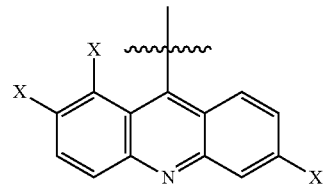
(A-i-91) 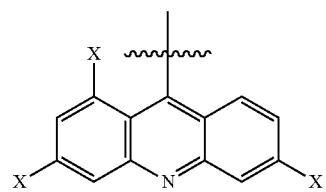
(A-i-92) 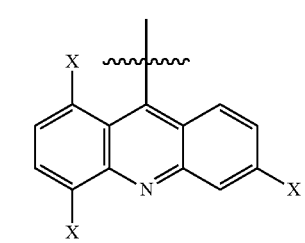
(A-i-93) 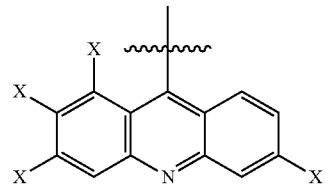
(A-i-94) 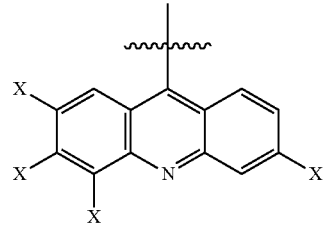
(A-i-95) 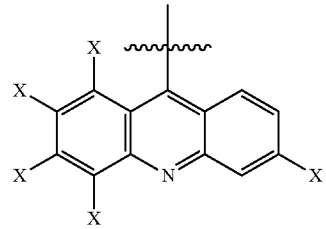
(A-i-96) 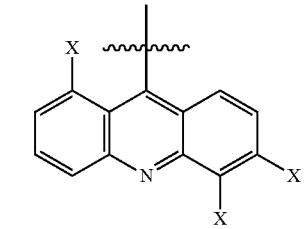
(A-i-97) 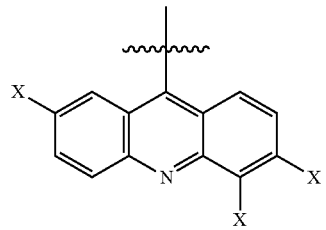
(A-i-98) 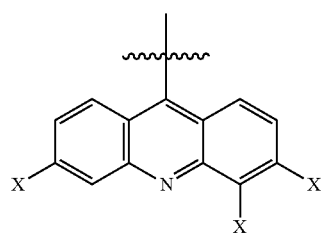
(A-i-99) 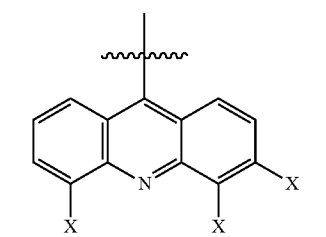
(A-i-100) 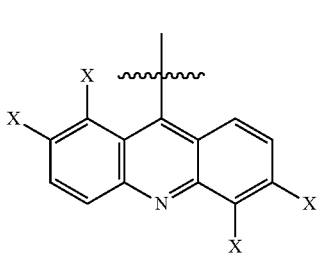
(A-i-101) 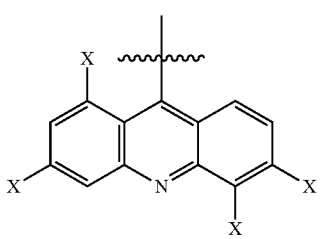
(A-i-102) 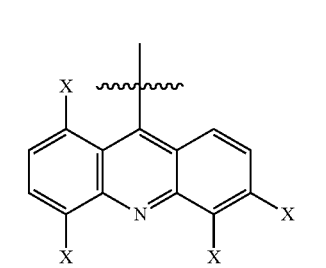

(A-i-103)
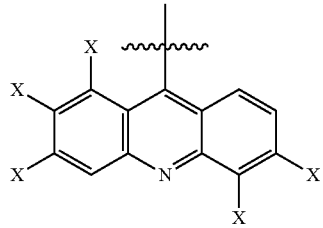

(A-i-104)
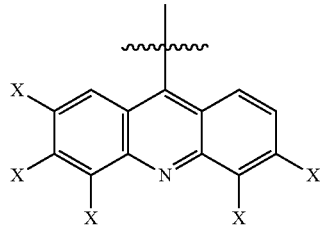

(A-i-105)
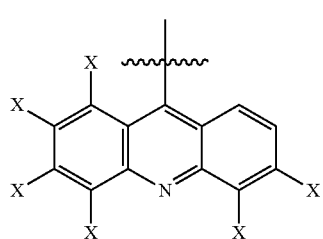

(A-i-106)
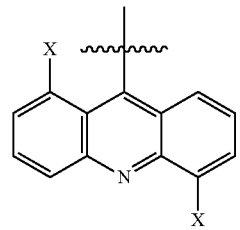

(A-i-107)
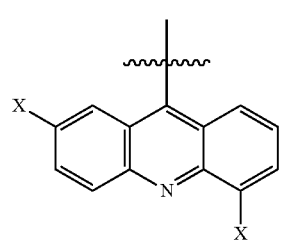

(A-i-108)
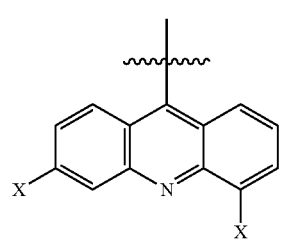

(A-i-109)
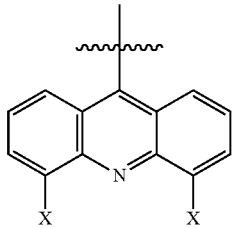

(A-i-110)
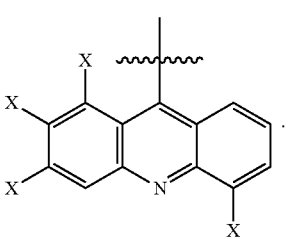

4. The TADF material of claim 2, wherein the electron donor group is represented by the following structural formula (D-i):

(D-i)
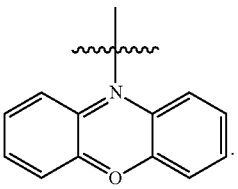

5. The TADF material of claim 2, wherein X is fluorine.

6. The TADF material of claim 2, wherein the electron acceptor is represented by structural formula (A-i-52).

7. The TADF material of claim 2, wherein the TADF material comprises the compound represented by one of the following structural formulas (I-1 to I-3):

(I-1)
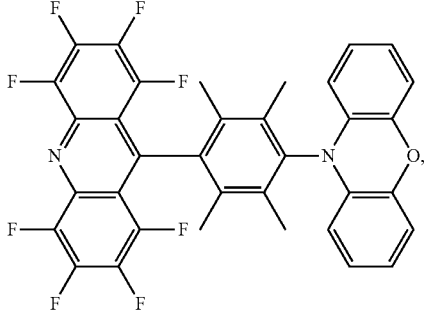

-continued

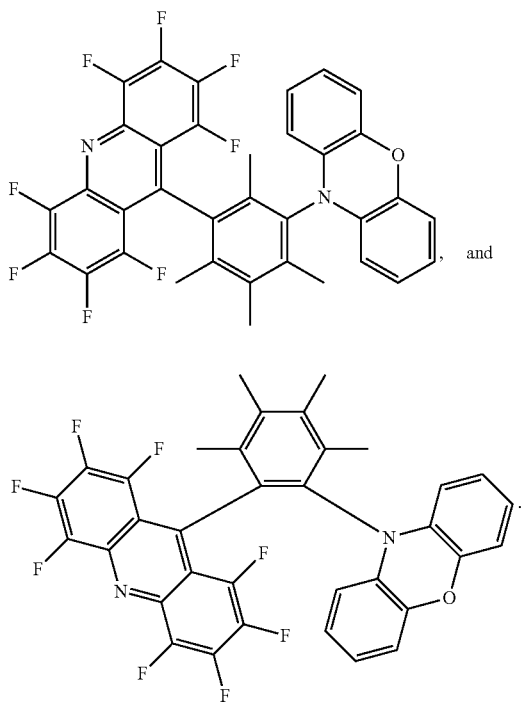

(I-2), and (I-3)

8. An organic electroluminescent (EL) device, comprising a first electrode, a second electrode, and at least one organic EL layer disposed between the first electrode and the second electrode, wherein the organic EL layer comprises the thermally activated delayed fluorescence (TADF) material of claim 1.

9. The organic EL device of claim 8, wherein the organic EL layer comprises a host material doped with the TADF material.

10. The organic EL device of claim 9, wherein a doping concentration of the TADF material is 3% to 5% by weight.

11. The organic EL device of claim 9, wherein the host material is 3, 3'-bis(N-carbazolyl)-1,1'-biphenyl.

12. The organic EL device of claim 8, wherein the organic EL device further comprises a hole injection layer disposed between first electrode and the organic EL layer, a hole transport layer disposed between the hole injection layer and the organic EL layer, and an electron transport layer disposed between the organic EL layer and the second electrode.

13. The organic EL device of claim 12, wherein the first electrode is an anode made of indium tin oxide; and
wherein the second electrode is a cathode made of aluminum or silver-magnesium alloy.

14. The organic EL device of claim 12, wherein the hole injection layer is made of molybdenum trioxide, poly(3,4-ethylenedioxythiophene)-polystyrenesulfonic acid (PEDOT:PSS), or polythiophene.

15. The organic EL device of claim 12, wherein the hole transport layer is made of an aromatic diamine compound, a triphenylamine compound, or an aromatic triamine compound.

16. The organic EL device of claim 12, wherein the electron transport layer is made of 1,3,5-tris(3-(3-pyridyl)phenyl)benzene.

17. The organic EL device of claim 12, wherein the electron injection layer is made of lithium fluoride.

18. A display panel, comprising the organic electroluminescent (EL) device of claim 8.

19. The display panel of claim 18, wherein the display panel further comprises a substrate, and the organic EL device is disposed on the substrate.

* * * * *